US012721282B2

(12) United States Patent
Bae et al.

(10) Patent No.: US 12,721,282 B2
(45) Date of Patent: Sep. 1, 2026

(54) **MICROBIAL COMPOSITION FOR ENHANCING THE INOCULATION RATE OF *TRICHOLOMA MATSUTAKE* MYCELIUM AND USE THEREOF**

(71) Applicant: NATIONAL INSTITUTE OF FOREST SCIENCE, Seoul (KR)

(72) Inventors: Eun Kyoung Bae, Gyeonggi-do (KR); Min Jeong Kang, Gyeonggi-do (KR); Eung Jun Park, Gyeonggi-do (KR)

(73) Assignee: NATIONAL INSTITUTE OF FOREST SCIENCE, Seoul (KR)

( * ) Notice: Subject to any disclaimer, the term of this patent is extended or adjusted under 35 U.S.C. 154(b) by 0 days.

(21) Appl. No.: 19/393,896

(22) Filed: Nov. 19, 2025

(65) Prior Publication Data

US 2026/0144195 A1 May 28, 2026

(30) Foreign Application Priority Data

Nov. 27, 2024 (KR) ........................ 10-2024-0171836

(51) Int. Cl.

| | |
|---|---|
| ***A01G 7/06*** | (2006.01) |
| ***A01G 18/00*** | (2018.01) |
| ***C12N 1/20*** | (2006.01) |

(52) U.S. Cl.

CPC *A01G 7/06* (2013.01); *C12N 1/20* (2013.01)

(58) Field of Classification Search

CPC .......... A01G 7/06; A01G 18/00; A01G 18/10; A01G 18/20; A01G 18/50; A01N 63/30; C12N 1/14; C12N 1/20

See application file for complete search history.

(56) References Cited

U.S. PATENT DOCUMENTS

| | | | | |
|---|---|---|---|---|
| 4,345,403 | A * | 8/1982 | Giovannetti | A01G 18/10 504/117 |
| 5,178,642 | A * | 1/1993 | Janerette | A01N 63/30 435/911 |
| 6,907,691 | B2 * | 6/2005 | Miller | A01G 18/00 47/1.1 |
| 6,951,074 | B2 * | 10/2005 | Miller | A01G 18/00 47/1.1 |
| 7,269,923 | B2 | 9/2007 | Park et al. | |
| 2006/0048444 | A1 * | 3/2006 | Kitagou | A01G 18/40 47/1.1 |

FOREIGN PATENT DOCUMENTS

| | | | | |
|---|---|---|---|---|
| CN | 108260470 | A * | 7/2018 | C12Q 1/6895 |
| JP | 3057676 | B2 | 7/2000 | |
| JP | 2004129653 | A * | 4/2004 | A01H 4/005 |
| JP | 2005052088 | A * | 3/2005 | C05F 11/00 |
| KR | 10-0390048 | B1 | 7/2003 | |
| KR | 10-1127514 | B1 | 6/2012 | |
| KR | 101569282 | B1 * | 11/2015 | C12N 1/14 |

* cited by examiner

*Primary Examiner* — Monica L Perry

(74) *Attorney, Agent, or Firm* — Harness, Dickey & Pierce, P.L.C.

(57) ABSTRACT

There is provided a microbial composition comprising *Paenibacillus cineris* and *Micrococcus* sp. for enhancing the inoculation rate of *T. matsutake* mycelium in trees, as well as a use thereof. The microbial composition according to the present invention significantly increases the inoculation rate of *T. matsutake* mycelium in trees. Furthermore, the composition does not inhibit the growth of *T. matsutake* mycelium and effectively suppresses harmful microorganisms that interfere with mycelium growth. The microbial composition of the present invention also remarkably improves the survival rate of *T. matsutake*-inoculated seedlings. According to the method for producing *T. matsutake* mycelium-inoculated seedlings of the present invention, seedlings with a high inoculation rate of *T. matsutake* mycelium and a high survival rate can be mass-produced and supplied in large quantities to mushroom cultivators.

5 Claims, 5 Drawing Sheets

Specification includes a Sequence Listing.

| Inhibition | 44 | 48 | 49 |
|---|---|---|---|
| 330 | | | 0.3/0.2 |
| 513 | 0.1/0.1 | 0.4/0.3 | 0.6/0.5 |
| 794 | | | 0.3/0.2 |
| 885 | | 0.2/0.1 | 0.2/0.1 |
| 1030 | | | 0.1/0.1 |
| 1038 | 0.5/0.6 | 0.6/0.6 | 0.5/0.5 |
| 1076 | | | 1.9/0.4 |
| 1519 | | 0.3/0.2 | |
| | | | |
| | 2 | 4 | 7 |
| Inhibiting 3 harmful strains | 2 | | |
| Inhibiting 2 harmful strains | 1 | | |
| Inhibiting 1 harmful strain | 5 | | |

FIG. 4

>Paenibacillus cineris 44
TAGACTTCACCCCCATCATCTACCCCACCTTCGGCGGCTGGCTCCTTGCGGTTACCTCAC
CGACTTCGGGTGTTGTAAACTCTCGTGGTGTGACGGGCGGTGTGTACAAGACCCGGGAAC
GTATTCACCGCGGCATGCTGATCCGCGATTACTAGCAATTCCGACTTCATGCAGGCGAGT
TGCAGCCTGCAATCCGAACTGAGACCAGCTTTGATAGGATTGGCTCCACCTCGCGGCTTC
GCTTCCCGTTGTACTGGCCATTGTAGTACGTGTGTAGCCCAGGTCATAAGGGGCATGATG
ATTTGACGTCATCCCCGCCTTCCTCCGGTTTGTCACCGGCAGTCATTCTAGAGTGCCCAC
CCGAAGTGCTGGCAACTAAAATCAAGGGTTGCGCTCGTTGCGGGACTTAACCCAACATCT
CACGACACGAGCTGACGACAACCATGCACCACCTGTCTCCTCTGTCCCGAAGGAAAGGTA
CATCTCTAGACCGGTCAGAGGGATGTCAAGACCTGGTAAGGTTCTTCGCGTTGCTTCGAA
TTAAACCACATACTCCACTGCTTGTGCGGGTCCCCGTCAATTCCTTTGAGTTTCAGTCTT
GCGACCGTACTCCCCAGGCGGAATGCTTAATGTGTTAACTTCGGCACCAAGGGTATCGAA
ACCCCTAACACCTAGCATTCATCGTTTACGGCGTGGACTACCAGGGTATCTAATCCTGTT
TGCTCCCCACGCTTTCGCGCCTCAGCGTCAGTTACAGCCCAGAGAGTCGCCTTCGCCACT
GGTGTTCCTCCACATATCTACGCATTTCACCGCTACACGTGGAATTCCACTCTCCTCTTC
TGCACTCAAGTCACCCAGTTTCCAGTGCGAACCAAGGTTGAGCCTTGGCCTTAAACACCA
GACTTAAATGACCGCCTGCGCGCGCTTTACGCCCAATAATTCCGGACAACGCTTGCCCCC
TACGTATTACCGCGGCTGCTGGCACGTAGTTAGCCGGGGCTTTCTTCTCAGGTACCGTCA
CTCCGATAGCAGTTACTCTACCGGACGTTCTTCCTGGCAACAGAGCTTTACGATCCGAAA
ACTTCATCACTCACGCGGCGTTGCTCCGTCAGCTTTCGCCATTGCGGAAGATTCCT >Micrococcus sp. 48
TAGACTTAGTCCCAATCGCTGGTCCCACCTTCGACGGCTCCCCCCACAAGGGTTAGGCCA
CCGGCTTCGGGTGTTACCGACTTTCGTGACTTGACGGGCGGTGTGTACAAGGCCCGGGAA
CGTATTCACCGCAGCGTTGCTGATCTGCGATTACTAGCGACTCCGACTTCATGGGGTCGA
GTTGCAGACCCCAATCCGAACTGAGACCGGCTTTTTGGGATTAGCTCCACCTCACAGTAT
CGCAACCCATTGTACCGGCCATTGTAGCATGCGTGAAGCCCAAGACATAAGGGGCATGAT
GATTTGACGTCGTCCTCACCTTCCTCCGAGTTGACCCCGGCAGTCTCCCATGAGTCCCCA
CCATTACGTGCTGGCAACATGGAACGAGGGTTGCGCTCGTTGCGGGACTTAACCCAACAT
CTCACGACACGAGCTGACGACAACCATGCACCACCTGTGAACCCGCCCCAAAGGGGAAAC
CGTATCTCTACGGCGATCGAGAACATGTCAAGCCTTGGTAAGGTTCTTCGCGTTGCATCG
AATTAATCCGCATGCTCCGCCGCTTGTGCGGGCCCCCGTCAATTCCTTTGAGTTTTAGCC
TTGCGGCCGTACTCCCCAGGCGGGGCACTTAATGCGTTAGCTGCGGCGCGGAAACCGTGG
AATGGTCCCCACACCTAGTGCCCAACGTTTACGGCATGGACTACCAGGGTATCTAATCCT
GTTCGCTCCCCATGCTTTCGCTCCTCAGCGTCAGTTACAGCCCAGAGACCTGCCTTCGCC
ATCGGTGTTCCTCCTGATATCTGCGCATTCCACCGCTACACCAGGAATTCCAGTCTCCCC
TACTGCACTCTAGTCTGCCCGTACCCACCGCAGATCCGGGGTTAAGCCCCGGACTTTCAC
GACAGACGCGACAAACCGCCTACGAGCTCTTTACGCCCAATAATTCCGGATAACGCTCGC
ACCCTACGTATTACCGCGGCTGCTGGCACGTAGTTAGCCGGTGCTTCTTCTGCAGGTACC
GTCACTTTCGCTTCTTCCCTACTGAAAGAGGTTTACAACCCGAAGGCCGTCATCCCTCAC
GCGGCGTCGCTGCATCAGGCTTGCGCCCATTGTGCAATATTCCCCACTGCTGCCTCCCGT
AGGAGTCTGGGCCGTGTCTCAGTCCCAGTGTGGCCGGTCACCCTCTCAGGCCGGCTACCC
GTCGTCGCCTTGGTGAGCCATTACCTCACCAACAAGCTGATAGGCCGCGAGTCCATCCAA
AACCGATAAATCTTTCCAACACCCACCATGCGGTAGGCGCTCCTATCCGGTATTAGACCC
AGTTTCCCAGGCTTATCCCAGAGTTAAGGGCAGGTTACTCACGTGTTACTCACCCGTTCG
CCACTAATCCACCCAGCAAGCTGGGCTTCATCGTTCGACTTGCATGTGTTAAGCACGCCG
CCGGCGTTCATCCTGAGCA >Paenibacillus cineris. 49
TTCACCCCCAATCATCTACCCCACCTTCGGCGGCTGGCTCCTTGCGGTTACCTCACCGAC
TTCGGGTGTTGTAAACTCTCGTGGTGTGACGGGCGGTGTGTACAAGACCCGGGAACGTAT
TCACCGCGGCATGCTGATCCGCGATTACTAGCAATTCCGACTTCATGCAGGCGAGTTGCA
GCCTGCAATCCGAACTGAGACCAGCTTTGATAGGATTGGCTCCACCTCGCGGCTTCGCTT
CCCGTTGTACTGGCCATTGTAGTACGTGTGTAGCCCAGGTCATAAGGGGCATGATGATTT
GACGTCATCCCCGCCTTCCTCCGGTTTGTCACCGGCAGTCATTCTAGAGTGCCCACCCGA
AGTGCTGGCAACTAAAATCAAGGGTTGCGCTCGTTGCGGGACTTAACCCAACATCTCACG
ACACGAGCTGACGACAACCATGCACCACCTGTCTCCTCTGTCCCGAAGGAAAGGTACATC
TCTAGACCGGTCAGAGGGATGTCAAGACCTGGTAAGGTTCTTCGCGTTGCTTCGAATTAA
ACCACATACTCCACTGCTTGTGCGGGTCCCCGTCAATTCCTTTGAGTTTCAGTCTTGCGA
CCGTACTCCCCAGGCGGAATGCTTAATGTGTTAACTTCGGCACCAAGGGTATCGAAACCC
CTAACACCTAGCATTCATCGTTTACGGCGTGGACTACCAGGGTATCTAATCCTGTTTGCT
CCCCACGCTTTCGCGCCTCAGCGTCAGTTACAGCCCAGAGAGTCGCCTTCGCCACTGGTG
TTCCTCCACATATCTACGCATTTCACCGCTACACGTGGAATTCCACTCTCCTCTTCTGCA
CTCAAGTCACCCAGTTTCCAGTGCGAACCAAGGTTGAGCCTTGGCCTTAAACACCAGACT
TAAATGACCGCCTGCGCGCGCTTTACGCCCAATAATTCCGGACAACGCTTGCCCCCTACG
TATTACCGCGGCTGCTGGCACGTAGTTAGCCGGGGCTTTCTTCTCAGGTACCGTCACTCC
GATAGCAGTACTCTACCGGACGTTCTTCCCTGGCAACAGAGCTTTACGATCCGAAAACCT
TCATCACTCACGCGG DTm3_2001F DTm3_2001R

| 18S | ITS1 | 5.8S | ITS2 | 28S |
|---|---|---|---|---|

| Name | Volume(uL) |
|---|---|
| DNA | 1 |
| 10x buffer | 2 |
| dNTP (2.5mM each) | 1.8 |
| Primer (10pmol) F | 0.5 |
| Primer (10pmol) R | 0.5 |
| Taq polymerase | 0.1 |
| DW | 14.1 |

| Degree (°C) | Time (min) |
|---|---|
| 95 | 5 |
| 95 | 0.5 |
| 64(DTm3) | 0.5/ 40x |
| 72 | 0.5 |
| 72 | 5 |
| 12 | ∞ |

```
                              SEQUENCE LISTING


Sequence total quantity: 9
SEQ ID NO: 1              moltype = DNA  length = 1136
FEATURE                   Location/Qualifiers
source                    1..1136
                          mol_type = genomic DNA
                          organism = Paenibacillus cineris
SEQUENCE: 1
tagacttcac ccccatcatc taccccacct tcggcggctg gctccttgcg gttacctcac  60
cgacttcggg tgttgtaaac tctcgtggtg tgacgggcgg tgtgtacaag acccgggaac  120
gtattcaccg cggcatgctg atccgcgatt actagcaatt ccgacttcat gcaggcgagt  180
tgcagcctgc aatccgaact gagaccagct ttgataggat tggctccacc tcgcggcttc  240
gcttcccgtt gtactggcca ttgtagtacg tgtgtagccc aggtcataag gggcatgatg  300
atttgacgtc atccccgcct tcctccggtt tgtcaccggc agtcattcta gagtgcccac  360
ccgaagtgct ggcaactaaa atcaagggtt gcgctcgttg cgggacttaa cccaacatct  420
cacgacacga gctgacgaca accatgcacc acctgtctcc tctgtcccga aggaaaggta  480
catctctaga ccggtcagag ggatgtcaag acctggtaag gttcttcgcg ttgcttcgaa  540
ttaaaccaca tactccactg cttgtgcggg tccccgtcaa ttcctttgag tttcagtctt  600
gcgaccgtac tccccaggcg gaatgcttaa tgtgttaact tcggcaccaa gggtatcgaa  660
acccctaaca cctagcattc atcgtttacg gcgtggacta ccagggtatc taatcctgtt  720
tgctccccac gctttcgcgc ctcagcgtca gttacagccc agagagtcgc cttcgccact  780
ggtgttcctc cacatatcta cgcatttcac cgctacacgt ggaattccac tctcctcttc  840
tgcactcaag tcacccagtt tccagtgcga accaaggttg agccttggcc ttaaacacca  900
gacttaaatg accgcctgcg cgcgctttac gcccaataat tccggacaac gcttgccccc  960
tacgtattac cgcggctgct ggcacgtagt tagccggggc tttcttctca ggtaccgtca  1020
ctccgatagc agttactcta ccggacgttc ttcctggcaa cagagcttta cgatccgaaa  1080
acttcatcac tcacgcggcg ttgctccgtc agctttcgcc attgcggaag attcct      1136

SEQ ID NO: 2              moltype = DNA  length = 1459
FEATURE                   Location/Qualifiers
source                    1..1459
                          mol_type = genomic DNA
                          organism = Micrococcus sp.
SEQUENCE: 2
tagacttagt cccaatcgct ggtcccacct tcgacggctc cccccacaag ggttaggcca  60
ccggcttcgg gtgttaccga ctttcgtgac ttgacgggcg gtgtgtacaa ggcccgggaa  120
cgtattcacc gcagcgttgc tgatctgcga ttactagcga ctccgacttc atggggtcga  180
gttgcagacc ccaatccgaa ctgagaccgg ctttttggga ttagctccac ctcacagtat  240
cgcaacccat tgtaccggcc attgtagcat gcgtgaagcc caagacataa ggggcatgat  300
gatttgacgt cgtcctcacc ttcctccgag ttgaccccgg cagtctccca tgagtcccca  360
ccattacgtg ctggcaacat ggaacgaggg ttgcgctcgt tgcgggactt aacccaacat  420
ctcacgacac gagctgacga caaccatgca ccacctgtga acccgcccca aaggggaaac  480
cgtatctcta cggcgatcga gaacatgtca agccttggta aggttcttcg cgttgcatcg  540
aattaatccg catgctccgc cgcttgtgcg ggcccccgtc aattcctttg agttttagcc  600
ttgcggccgt actccccagg cggggcactt aatgcgttag ctgcggcgcg gaaaccgtgg  660
aatggtcccc acacctagtg cccaacgttt acggcatgga ctaccagggt atctaatcct  720
gttcgctccc catgctttcg ctcctcagcg tcagttacag cccagagacc tgccttcgcc  780
atcggtgttc ctcctgatat ctgcgcattc caccgctaca ccaggaattc cagtctcccc  840
tactgcactc tagtctgccc gtacccaccg cagatccggg gttaagcccc ggactttcac  900
gacagacgcg acaaaccgcc tacgagctct ttacgcccaa taattccgga taacgctcgc  960
accctacgta ttaccgcggc tgctggcacg tagttagccg gtgcttcttc tgcaggtacc  1020
gtcactttcg cttcttccct actgaaagag gtttacaacc cgaaggccgt catccctcac  1080
gcggcgtcgc tgcatcaggc ttgcgcccat tgtgcaatat tccccactgc tgcctcccgt  1140
aggagtctgg gccgtgtctc agtcccagtg tggccggtca ccctctcagg ccggctaccc  1200
gtcgtcgcct tggtgagcca ttacctcacc aacaagctga taggccgcga gtccatccaa  1260
aaccgataaa tctttccaac acccaccatg cggtaggcgc tcctatccgg tattagaccc  1320
agtttcccag gcttatccca gagttaaggg caggttactc acgtgttact cacccgttcg  1380
ccactaatcc acccagcaag ctgggcttca tcgttcgact tgcatgtgtt aagcacgccg  1440
ccggcgttca tcctgagca                                               1459

SEQ ID NO: 3              moltype = DNA  length = 1095
FEATURE                   Location/Qualifiers
source                    1..1095
                          mol_type = genomic DNA
                          organism = Paenibacillus cineris
SEQUENCE: 3
ttcaccccca atcatctacc ccaccttcgg cggctggctc cttgcggtta cctcaccgac  60
ttcgggtgtt gtaaactctc gtggtgtgac gggcggtgtg tacaagaccc gggaacgtat  120
tcaccgcggc atgctgatcc gcgattacta gcaattccga cttcatgcag gcgagttgca  180
gcctgcaatc cgaactgaga ccagctttga taggattggc tccacctcgc ggcttcgctt  240
cccgttgtac tggccattgt agtacgtgtg tagcccaggt cataaggggc atgatgattt  300
```

-continued

```
gacgtcatcc ccgccttcct ccggtttgtc accggcagtc attctagagt gcccacccga  360
agtgctggca actaaaatca agggttgcgc tcgttgcggg acttaaccca acatctcacg  420
acacgagctg acgacaacca tgcaccacct gtctcctctg tcccgaagga aaggtacatc  480
tctagaccgg tcagagggat gtcaagacct ggtaaggttc ttcgcgttgc ttcgaattaa  540
accacatact ccactgcttg tgcgggtccc cgtcaattcc tttgagtttc agtcttgcga  600
ccgtactccc caggcggaat gcttaatgtg ttaacttcgg caccaagggt atcgaaaccc  660
ctaacaccta gcattcatcg tttacggcgt ggactaccag ggtatctaat cctgtttgct  720
ccccacgctt tcgcgcctca gcgtcagtta cagcccagag agtcgccttc gccactggtg  780
ttcctccaca tatctacgca tttcaccgct acacgtggaa ttccactctc ctcttctgca  840
ctcaagtcac ccagtttcca gtgcgaacca aggttgagcc ttggccttaa acaccagact  900
taaatgaccg cctgcgcgcg ctttacgccc aataattccg gacaacgctt gccccctacg  960
tattaccgcg gctgctggca cgtagttagc cggggctttc ttctcaggta ccgtcactcc  1020
gatagcagta ctctaccgga cgttcttccc tggcaacaga gctttacgat ccgaaaacct  1080
tcatcactca cgcgg                                                   1095

SEQ ID NO: 4            moltype = DNA  length = 20
FEATURE                 Location/Qualifiers
source                  1..20
                        mol_type = other DNA
                        organism = synthetic construct
SEQUENCE: 4
agagtttgat cmtggctcag                                              20

SEQ ID NO: 5            moltype = DNA  length = 18
FEATURE                 Location/Qualifiers
source                  1..18
                        mol_type = other DNA
                        organism = synthetic construct
SEQUENCE: 5
ggattagata ccctggta                                                18

SEQ ID NO: 6            moltype = DNA  length = 20
FEATURE                 Location/Qualifiers
source                  1..20
                        mol_type = other DNA
                        organism = synthetic construct
SEQUENCE: 6
ccgtcaattc ctttragttt                                              20

SEQ ID NO: 7            moltype = DNA  length = 20
FEATURE                 Location/Qualifiers
source                  1..20
                        mol_type = other DNA
                        organism = synthetic construct
SEQUENCE: 7
cggttacctt gttacgactt                                              20

SEQ ID NO: 8            moltype = DNA  length = 28
FEATURE                 Location/Qualifiers
source                  1..28
                        mol_type = other DNA
                        organism = synthetic construct
SEQUENCE: 8
aatatgtctc gaggaagctc ggtttgag                                     28

SEQ ID NO: 9            moltype = DNA  length = 24
FEATURE                 Location/Qualifiers
source                  1..24
                        mol_type = other DNA
                        organism = synthetic construct
SEQUENCE: 9
agcctgcaac aactcccaaa atcc                                         24
```

MICROBIAL COMPOSITION FOR ENHANCING THE INOCULATION RATE OF *TRICHOLOMA MATSUTAKE* MYCELIUM AND USE THEREOF

CROSS-REFERENCE TO RELATED APPLICATIONS

This application claims benefit of and priority to Korean Patent Application No. 10-2024-0171836, filed on Nov. 27, 2024. The entire disclosure of the application identified in this paragraph is incorporated herein by reference.

SEQUENCE LISTING

This application contains references to amino acid sequences and/or nucleic acid sequences which have been submitted concurrently herewith as the sequence listing XML file entitled "000008us_SequenceListing.XML", file size 12,677 bytes, created on 18 Nov. 2025. The aforementioned sequence listing is hereby incorporated by reference in its entirety pursuant to 37 C.F.R. § 1.52(e)(5).

FIELD

The present invention relates to a microbial composition for enhancing the inoculation rate of *Tricholoma matsutake* mycelium and the use thereof, and more particularly, to a microbial composition that enhances the inoculation rate of *T. matsutake* mycelium in trees, a formulation for enhancing the inoculation rate of *T. matsutake* mycelium in trees comprising the microbial composition, a method for enhancing the inoculation rate of *T. matsutake* mycelium in trees using the composition, and a method for producing *T. matsutake* mycelium-inoculated seedlings.

BACKGROUND

Pine mushroom (Matsutake; *Tricholoma matsutake*) is a fungus belonging to the family Tricholomataceae of the order Agaricales, and is collected around coniferous forests such as pine (*Pinus densiflora*), Siberian dwarf pine (*Pinus pumila*), Manchurian fir (*Abies holophylla*), or Yezo spruce (*Picea jezoensis*). In Korea, it is known to occur mainly in pine forests. The pine mushroom is a highly valued edible mushroom preferred in Korea and Japan, and is an important source of income for farmers, particularly in the eastern coastal regions of Korea.

*T. matsutake* forms ectomycorrhizae with the roots of pine trees. Typically, *T. matsutake* is found in pine forests aged between 20 and 60 years. The mycelium of the fungus colonizes the fine roots of pine trees, forming ectomycorrhizal associations and acting as a biotrophic symbiont. After the spores of *T. matsutake* germinate under suitable environmental conditions, the resulting mycelium colonizes the fine roots of pine trees. The living fine roots, which are white or pale yellow in color, gradually turn dark brown as they develop into mature ectomycorrhizae. The ectomycorrhiza grows and propagates underground in a cushion-like form, forming small white colonies referred to as "patches." These patches expand outward in a circular pattern, which is called a "fairy ring." When the underground temperature remains below 19° C. for 5 to 7 days, the well-developed mycelium begin to produce fruiting bodies.

Since *T. matsutake* is an obligate symbiotic fungus, artificial fruiting is extremely difficult, and cultivation by artificial means has not been successful. Accordingly, in order to improve the yield of *T. matsutake*, various methods have been employed, such as spreading the cultured mycelium of *T. matsutake* onto natural fruiting grounds and incorporating mycelium aggregates into the soil; recovering spores from the fruiting bodies of *T. matsutake* and dispersing them over the fruiting sites; and transplanting soil containing viable mycelium to areas where *T. matsutake* has not been observed. However, due to the characteristic of *T. matsutake* mycelium having a slower growth rate than other bacteria and fungi, the mycelium lost their vitality and, depending on rainfall and soil conditions, failed to colonize the roots of pine trees and were washed away. Consequently, no significant increase in the yield of *T. matsutake* was obtained. As another approach, a method of producing *T. matsutake*-infected seedlings has been attempted, in which pine seedlings are planted near the fairy ring of *T. matsutake* to obtain infected seedlings for transplantation. However, the success rate of this method remains low, and there is a continuing need for the development of improved techniques.

PRIOR ART REFERENCES

Korean Patent No. 10-1127514
Japanese Patent No. 3057676
Korean Patent No. 10-0390048

SUMMARY

Problems to be Solved by the Invention

In order to address the above problems, the inventors of the present invention conducted intensive research and found that a microbial composition comprising *Paenibacillus cineris* and *Micrococcus* sp. significantly enhances the inoculation rate of *T. matsutake* mycelium in pine trees and also improves the survival rate of inoculated pine seedlings. Based on this discovery, the present invention was completed.

Accordingly, an object of the present invention is to provide a microbial composition comprising *Paenibacillus cineris* and *Micrococcus* sp. that enhances the inoculation rate of *T. matsutake* mycelium in trees.

Another object of the invention is to provide a formulation for enhancing the inoculation rate of *T. matsutake* mycelium in trees, comprising the above microbial composition as an active ingredient.

A further object of the invention is to provide a method for enhancing the inoculation rate of *T. matsutake* mycelium in trees using the above microbial composition or formulation.

Another object of the invention is to provide a method for producing *T. matsutake* mycelium-inoculated seedlings using the above microbial composition or formulation.

Means for Solving the Problems

To achieve the above objects, the present invention provides a microbial composition for enhancing the inoculation rate of *T. matsutake* mycelium in trees, comprising *Paenibacillus cineris* and *Micrococcus* sp.

The term "tree" as used herein refers to tree species capable of forming symbiotic associations with *T. matsutake*, including pine (*Pinus densiflora*), Siberian dwarf pine (*Pinus pumila*), Manchurian fir (*Abies holophylla*), or Yezo spruce (*Picea jezoensis*), with pine being the primary host species in Korea.

The term "Inoculation" refers to the process of infecting a tree directly with *T. matsutake* mycelium. The terms "*T. matsutake* mycelium" and "*T. matsutake*" are used interchangeably herein.

During research on enhancing *T. matsutake* inoculation in pine trees, the inventors isolated three bacterial strains—NIFoS B_44 (44), NIFoS B_48 (48), and NIFoS B_49 (49)—from coniferous forest soil. These strains promote the growth of *T. matsutake* mycelium, inhibit harmful bacteria detrimental to *T. matsutake* growth, and enhance inoculation rates in pine roots (see FIG. 1*b*).

Sequencing of the 16S rRNA regions to identify the three strains isolated in the present invention revealed that two of the isolates belong to *Paenibacillus cineris*, while the remaining one belongs to *Micrococcus* sp. Accordingly, the strains were designated as *Paenibacillus cineris* 44 (NIFoS B_44), *Paenibacillus cineris* 49 (NIFoS B_49), and *Micrococcus* sp. 48 (NIFoS B_48) (see FIG. 4).

According to one embodiment of the present invention, it was confirmed that the three strains belonging to two bacterial species of the present invention significantly enhanced the inoculation rate of *T. matsutake* on pine trees (41.2%) (see FIG. 5 and Table 4). These results indicate that the two bacterial species discovered in the present invention can effectively increase the inoculation efficiency of *T. matsutake* mycelium. The two bacterial species did not inhibit the growth of *T. matsutake* mycelium, but exhibited an inhibitory effect on harmful microorganisms that suppress the growth of *T. matsutake* mycelium (see FIG. 3 and Table 1). Furthermore, the survival rate of inoculated pine seedlings with the two bacterial species increased remarkably (85%) (Table 5). Therefore, these two bacterial species can be effectively used as a microbial agent for enhancing the inoculation rate of *T. matsutake*.

In the microbial composition of the present invention, the microbes (*Paenibacillus cineris* and *Micrococcus* sp.) may be included in the form of viable cells, dead cells, dried cells, culture broth, or microbial pellets.

The microbial pellets may be obtained by centrifuging the cultured broth and removing the supernatant.

In the present invention, for stabilization, the microbial composition may be formulated into pellets, wettable powders, granules, or encapsulated formulations.

In the microbial composition of the present invention, *Paenibacillus cineris* and *Micrococcus* sp. may be mixed at a volume ratio of 2:1 to 1:2, preferably at a 2:1 ratio.

The two species may also be stored separately for long-term preservation and mixed immediately prior to use. For storage, two species can be preserved below-70° C. in glycerol storage solution or by freeze-drying at −20° C. to −80° C.

In the present invention, the wettable powder formulation may be prepared by drying and pulverizing the cultured medium, followed by mixing with surfactants and extenders/nutrients.

The granule formulation may be prepared by drying and pulverizing the inoculated medium, followed by adding surfactants, extenders/nutrients, and disintegrants.

In the present invention, the surfactants may be selected one or more from the group consisting of polycarboxylates, sodium lignosulfonate, calcium lignosulfonate, sodium dialkyl sulfosuccinate, sodium alkylaryl sulfonate, polyoxyethylene alkylphenyl ether, sodium tripolyphosphate, polyoxyethylene alkylaryl phosphate ester, polyoxyethylene alkylaryl ether, polyoxyethylene alkylaryl polymer, polyoxyalkylene alkylphenyl ether, polyoxyethylene nonylphenyl ether, sodium sulfonate naphthalene formaldehyde, Triton 100, and Tween 80. The extenders/nutrients may be selected one or more from the group consisting of soybean powder, rice, wheat, loess, diatomite, dextrin, glucose, and starch. The disintegrants may be selected one or more from the group consisting of bentonite, talc, dialite, kaolin, and calcium carbonate.

The granule formulation may further comprise one or more selected from surfactants, inert carriers, preservatives, wetting agents, dispersants, attractants, encapsulating agents, binders, emulsifiers, colorants, UV protectants, buffers, and flow agents.

According to another aspect of the present invention, there is provided a formulation for enhancing the inoculation rate of *T. matsutake* mycelium in trees, comprising the above microbial composition as an active ingredient. The formulation can be formulated as a plant nutrient composition or a soil conditioner composition.

The microbial composition can be applied by immersing (soaking) tree roots in a mixture of *T. matsutake* mycelium and the microbial composition, spraying the mixture onto roots, injecting or pouring the mixture around the roots of planted trees, or by other known microbial application methods.

According to another aspect of the invention, there is provided a method for enhancing the inoculation rate of *T. matsutake* mycelium in trees using the microbial composition described above.

According to yet another aspect of the invention, there is provided a method for producing *T. matsutake* mycelium-inoculated seedlings using the microbial composition described above.

The method comprises:

i) preparing a *T. matsutake* mycelium culture solution by liquid culturing the *T. matsutake* mycelium and homogenizing the culture using a homogenizer;

ii) culturing *Paenibacillus cineris* and *Micrococcus* sp. and centrifuging the cultures to obtain microbial pellets;

iii) washing and pruning the roots of pine seedlings;

iv) immersing the roots of the root-pruned pine seedlings in a mixed solution prepared by mixing the *T. matsutake* mycelium culture solution of step (i) and the microbial pellets of step (ii) to inoculate the seedlings; and v) planting the inoculated pine seedlings in soil and cultivating them.

The method may further include, if necessary, vi) an additional inoculation step in which, after planting the pine seedlings in soil, the mixed solution of the *T. matsutake* mycelium culture obtained in step (i) and the microbial pellets obtained in step (ii) is poured around the roots.

Step (i): Preparation of *T. matsutake* Mycelium Culture Solution

A *T. matsutake* mycelium culture solution is prepared by liquid culturing the *T. matsutake* mycelium and homogenizing the culture using a homogenizer.

The liquid culture of *T. matsutake* mycelium may be carried out by culturing the mycelium in TMB (*T. matsutake* broth; Glucose 20 g/L, Yeast extract 1.5 g/L, Soytone 1.5 g/L, pH 5.2) medium at 25° C. with shaking (150 rpm) for one month.

The *T. matsutake* mycelium used for the liquid culture can be obtained by culturing a stock mycelium stored on PDA (Potato Dextrose Agar, Difco 00980; Potato starch 4 g/L, Dextrose 20 g/L, Agar 15 g/L) slant medium on TMM (*T. matsutake* medium; Glucose 20 g/L, Yeast extract 1.5 g/L, Soytone 1.5 g/L, Agar 20 g/L, pH 5.2) solid medium at 25°

C. for one month. After sufficient growth, the cultured mycelium is finely chopped into pieces less than 5 mm using a sterilized scalpel and then transferred to PDB (Potato Dextrose Broth, Difco 254920; Potato starch 4 g/L, Dextrose 20 g/L) liquid medium, followed by shaking culture at 25° C. and 150 rpm for one month.

To increase the contact efficiency between pine roots and *T. matsutake* mycelium, the cultured mycelium is homogenized using a homogenizer to obtain a uniform size of approximately 1~2 mm.

Step (ii): Preparation of Microbial Pellets

*Paenibacillus cineris* and *Micrococcus* sp. are cultured and centrifuged to obtain microbial pellets.

The two microbes are separated from stored glycerol stocks, streaked on TSA (Tryptone Soy Agar; tryptone 17 g/L, soy peptone 3 g/L, NaCl 5 g/L, $K_2HPO_4$ 2.5 g/L, dextrose 2.5 g/L, agar 20 g/L) medium plates, and statically cultured at 26~30° C. for 2~3 days. A single colony is then selected and transferred into TSB (Tryptone Soy Broth; Pancreatic digest of casein 17 g/L, Papaic digest of soybean 3 g/L, dextrose 2.5 g/L, sodium chloride 5 g/L, dipotassium phosphate 2.5 g/L) and are cultured with shaking for 3 days. Then the cell density is adjusted to $OD_{600}$=0.1, followed by centrifugation of the culture at 3000~4000 rpm for 10 minutes. The supernatant is removed, and the resulting pellets are collected as microbial pellets.

Step (iii): Root Pruning of Pine Seedlings

The roots of pine seedlings are washed and pruned to prepare for inoculation.

Pine seedlings that are 1~2 years old (1-0 or 2-0 seedlings) grown in nursery soil can be used, though the invention is not limited thereto.

The washing may be performed by removing the nursery soil and rinsing the roots three or more times with tap water.

The washed roots are then pruned to a length of 15~20 cm, preferably about 16 cm, to facilitate inoculation with the *T. matsutake* mycelium and the microbes, while maintaining sufficient moisture to prevent drying of the root tips.

Step (iv): Inoculation of Pine Seedlings

The roots of the root-pruned pine seedlings are immersed in the mixed solution prepared by mixing the *T. matsutake* mycelium culture solution of step (i) and the microbial pellets of step (ii) to inoculate the seedlings.

The immersing is carried out for 20~40 minutes, preferably 30 minutes.

Step (v): Cultivation of Inoculated Pine Seedlings

The inoculated pine seedlings are planted in soil and cultivated.

The planted inoculated seedlings may be cultivated under conditions of 25~30° C. and 50% humidity, though the invention is not limited thereto.

Step (vi): Additional Inoculation

If necessary, after planting the inoculated pine seedlings in soil, the mixed solution of the *T. matsutake* mycelium culture obtained in step (i) and the microbial pellets obtained in step (ii) may be poured around the roots for additional inoculation.

The additional inoculation may be performed 2~3 times at two-week intervals after planting, though not limited thereto.

The inoculation volume may be 5~15 mL, preferably about 10 mL.

According to the method for producing *T. matsutake* mycelium-inoculated seedlings of the present invention, both the inoculation rate of *T. matsutake* mycelium and the survival rate of the inoculated seedlings are significantly enhanced.

Effects of the Invention

The microbial composition according to the present invention significantly improves the inoculation rate of *T. matsutake* mycelium in trees. In addition, the microbial composition does not inhibit the growth of *T. matsutake* mycelium, but rather suppresses harmful microorganisms that inhibit its growth. Furthermore, the microbial composition significantly enhances the survival rate of *T. matsutake* mycelium-inoculated seedlings.

According to the method for producing *T. matsutake* mycelium-inoculated seedlings of the present invention, inoculated seedlings with high inoculation rates and survival rates can be mass-produced and supplied to farmers.

BRIEF DESCRIPTION OF DRAWINGS

FIG. 4 shows the nucleotide sequences of 16S rRNA genes of *Paenibacillus cineris* NIFoS B_44, *Paenibacillus. cineris* NIFoS B_49, and *Micrococcus* sp. NIFoS B_48.

DETAILED DESCRIPTION

Hereinafter, the configuration and effects of the present invention will be described in further detail through specific examples for better understanding. However, the following examples are provided merely for illustrative purposes to facilitate understanding of the invention, and the scope of the present invention is not limited thereto.

Example 1: Screening and Selection of Microbe Candidates

To screen for bacterial microbes that enhance the inoculation rate of *T. matsutake* (*matsutake* mycelium), microorganisms were isolated from the soil of fairy rings where *T. matsutake* naturally occurs and from the roots of pine trees growing in Suwon, Gyeonggi-do, South Korea.

Specifically, soil samples were collected from pine forests by removing the litter layer from the soil in fairy ring areas of *T. matsutake* and pine tree colony sites. The collected soil samples were diluted with sterilized water at a volume ratio of 10:1 (soil: water) in 50 mL falcon tubes, and then serially diluted at $1:10^{-3}\sim10^{-8}$. The diluted samples were spread on PDA and TSA agar plates.

Pine roots were surface-sterilized with 2% sodium hypochlorite (NaOCl), fragmented with a sterilized scalpel, and then plated on PDA and TSA media. As a result, a total of 436 strains were isolated, among which 412 strains inhibited the growth of *T. matsutake*, while 24 strains did not inhibit its growth.

Figure 1:
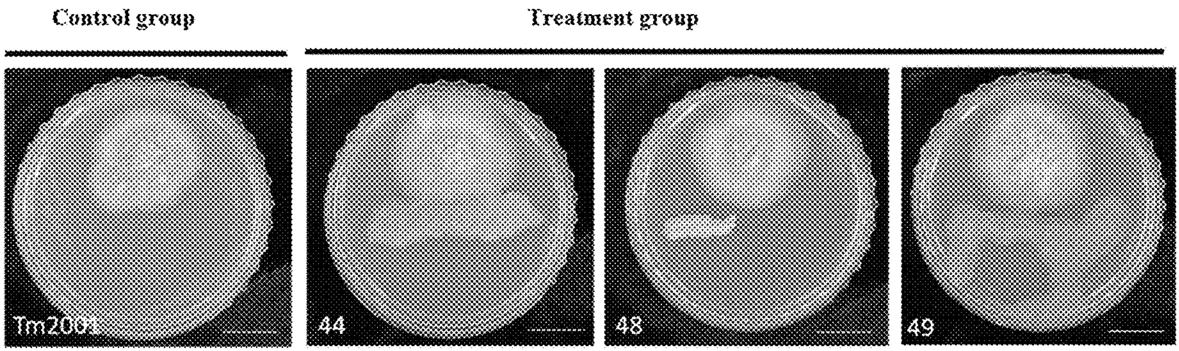
FIG. 1 shows the results of dual culture of *Paenibacillus cineris* NIFoS B_44, *Paenibacillus cineris* NIFoS B_49, and *Micrococcus* sp. NIFoS B_48 according to the present invention, with *T. matsutake* (NIFoS 2001).

The analysis of inhibitory activity against the growth of *T. matsutake* was performed using *T. matsutake* (NIFoS 2001). After culturing the *T. matsutake* mycelium on PDA medium at 24° C. for 25 days, a 5-mm mycelium disk was obtained using a cork borer and placed at the center of a disposable Petri dish containing PDA medium. Each isolated bacterial strain was then streaked at a distance of 1~2 mm from the mycelium disk, and dual cultivation was carried out (see FIG. 1).

Figure 2:
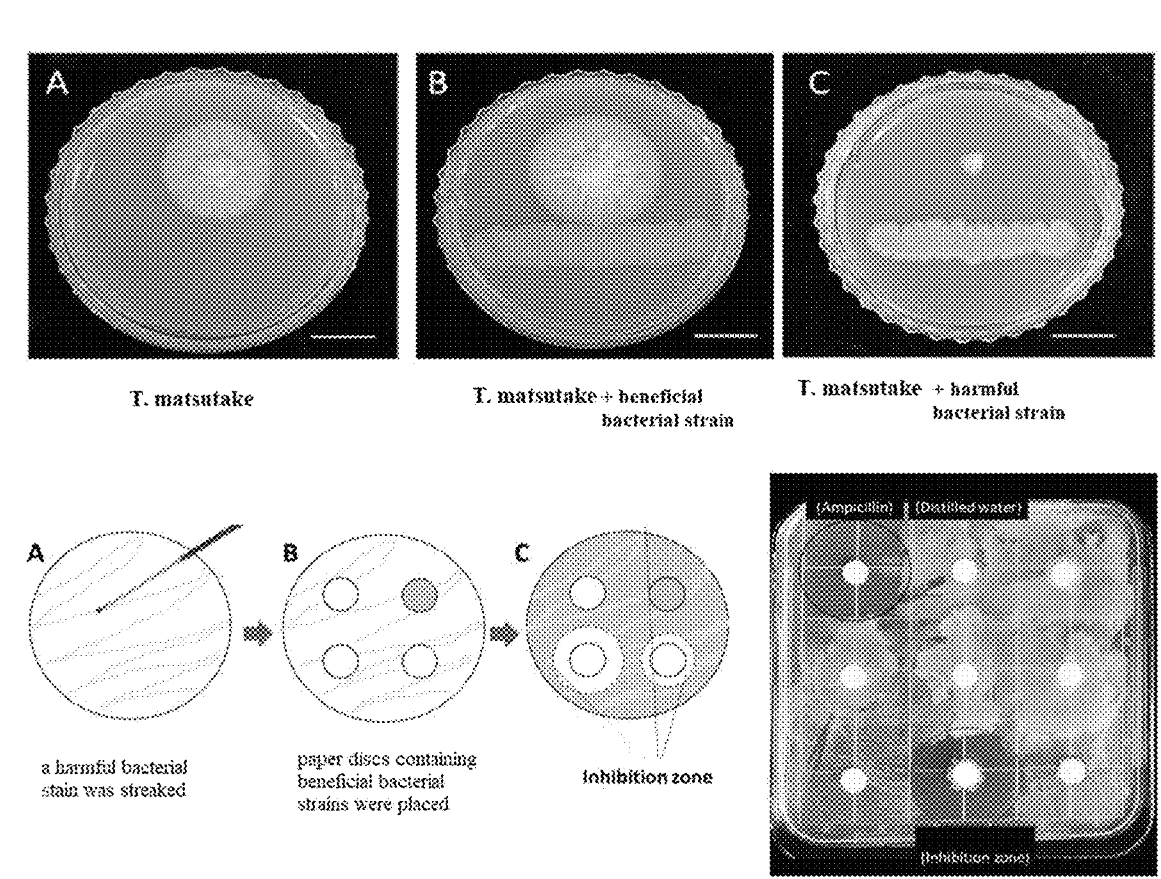
FIG. 2 shows the dual culture process for confirming the interactions between beneficial and harmful microorganisms with respect to *T. matsutake.*

To observe the interaction between harmful bacteria (that inhibit *T. matsutake* growth by more than 20%) and beneficial bacteria (that do not inhibit its growth), dual culture tests were performed. Specifically, a harmful bacterial stain was streaked on TSA (tryptone soy agar; tryptone 17 g/L, soy peptone 3 g/L, NaCl 5 g/L, $K_2HPO_4$ 2.5 g/L, dextrose 2.5 g/L, agar 20 g/L) medium, and paper discs containing beneficial bacterial strains were placed on the inoculated medium, to observe inter-strain interactions (FIG. 2).

Figure 3:
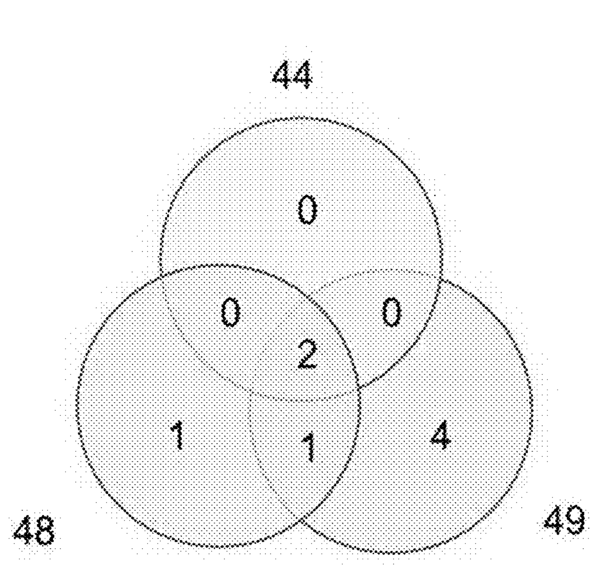
FIG. 3 shows the experimental results for analyzing whether *Paenibacillus cineris* NIFoS B_44, *Paenibacillus cineris* NIFoS B_49, and *Micrococcus* sp. NIFoS B_48 according to the present invention exhibit inhibitory effects against harmful microorganisms affecting *T. matsutake.*

When the beneficial bacterial stains inhibit the growth of the harmful bacterial strains, a transparent halo-shaped area, known as a clear zone (inhibition zone), can be observed. Based on such dual culture results, three bacterial strains exhibiting antagonistic effects against harmful microorganisms that inhibit the growth of *T. matsutake* were selected from the isolated strains (see FIG. 3 and Table 1).

TABLE 1

| Strain No. | Inhibiting 1 harmful strain | Inhibiting 2 harmful strains | Inhibiting 3 harmful strains | Inhibition rate (based on 412 harmful strains) | *T. matsutake* growth rate (%) |
|---|---|---|---|---|---|
| 44 | 0 | 0 | 2 | 0.5 | 100.4 |
| 48 | 1 | 1 | 2 | 1.0 | 103.0 |
| 49 | 4 | 1 | 2 | 1.7 | 99.7 |

Pure colonies of the three selected bacterial strains were obtained by streaking them onto TSA medium. The obtained pure colonies were inoculated into TSB (tryptone soy broth; pancreatic digest of casein 17 g/L, papaic digest of soybean 3 g/L, dextrose 2.5 g/L, sodium chloride 5 g/L, dipotassium phosphate 2.5 g/L) and incubated in a shaking incubator at 25° C., 200 rpm for 2 days. The resulting bacterial cultures were adjusted to a concentration of $10^8$ CFU/mL and preserved for further experiments by adding 20% (v/v) glycerol, followed by storage at −80° C.

Example 2: Identification of Selected Strains

The identification of the three bacterial strains 44, 48, and 49, selected in Example 1, was performed by Macrogen Co., Ltd. (Korea). For molecular identification of the bacterial strains, universal primers targeting the V1~V9 regions of the 16S rDNA were used. Specifically, combinations of the primers listed in Table 2 (27F [V1~V9 region], 785F [V5~V9 region], 907R [V1~V5 region], and 1492R [V1~V9 region]) were employed to analyze the 16S rRNA gene sequences of the three strains. The analyzed 16S rRNA gene sequences are shown in FIG. 4 and SEQ ID Nos. 1~3.

TABLE 2

| Primer name | Sequence (5'-3') | SEQ ID No. |
|---|---|---|
| 27F | AGAGTTTGATCMTGGCTCAG | 4 |
| 785F | GGATTAGATACCCTGGTA | 5 |
| 907R | CCGTCAATTCCTTTRAGTTT | 6 |
| 1492R | CGGTTACCTTGTTACGACTT | 7 |

Based on comparative analysis with publicly available microbial 16S rRNA gene sequences, which are most widely used for taxonomic identification, it was confirmed that the 16S rRNA gene sequences of strains 44 and 49 showed 99.55% and 99.81% sequence identity, respectively, with *Paenibacillus cineris*, and the 16S rRNA gene sequence of strain 48 showed 99.93% sequence identity with *Micrococcus* sp.

Based on these identification results, strains 44, 49, and 48 were designated as follows: *Paenibacillus cineris* NIFoS B_44, *Paenibacillus cineris* NIFoS B_49, and *Micrococcus* sp. NIFoS B_48, respectively.

Preparation Example 1: Cultivation of *T. matsutake* Mycelium and Preparation of the Inoculum Solution (*T. matsutake* Mycelium Culture Solution)

*T. matsutake* NIFoS 2001, isolated from wild *T. matsutake* collected in Yeongwol-gun, Korea, was used as the inoculum. The fungal strain was isolated from the fruiting body of *T. matsutake* and deposited in the NCBI Gene Bank (Accession No. GCA_026213095.1).

The *T. matsutake* strain, maintained as a stock on PDA (Potato Dextrose Agar, Difco 00980; Potato starch 4 g/L, Dextrose 20 g/L, Agar 15 g/L) slants, was subcultured on TMM medium (*T. matsutake* medium; Glucose 20 g/L, Yeast extract 1.5 g/L, Soytone 1.5 g/L, Agar 20 g/L, pH 5.2) at 25° C. for one month under stationary conditions. The well-grown *T. matsutake* mycelium were finely cut into pieces of 5 mm or less using a sterilized scalpel. The mycelium pieces were then transferred with sterilized forceps into PDB (Potato Dextrose Broth, Difco 254920: Potato starch 4 g/L, Dextrose 20 g/L) liquid medium and cultured with shaking at 25° C. and 150 rpm for 1 month. To prepare the inoculum for *T. matsutake*, the cultured mycelium was transferred to fresh TMB (*T. matsutake* broth; Glucose 20 g/L, Yeast extract 1.5 g/L, Soytone 1.5 g/L, pH 5.2) and shaken at 25° C. and 150 rpm for 1 month. The mycelium was then homogenized to a size of 1~2 mm using a homogenizer to prepare the *T. matsutake* mycelium culture solution. For the inoculum (*T. matsutake* mycelium culture solution) used, the biomass of the *T. matsutake* mycelium was prepared at 30~70 g per 500 mL.

Preparation Example 2: Cultivation of the Microbes of the Present Invention and Preparation of Microbial Inoculum (Microbial Pellets)

The three bacterial strains identified according to the invention were recovered from glycerol stock cultures and streaked on TSA (Tryptone Soy Agar; Tryptone 17 g/L, Soy peptone 3 g/L, NaCl 5 g/L, $K_2HPO_4$ 2.5 g/L, Dextrose 2.5 g/L, Agar 20 g/L) medium plates. The plates were statically cultured at 28° C. for 2 days to select single colonies. Each selected colony was then cultured in TSB (Tryptone Soy Broth; Pancreatic digest of casein 17 g/L, Papain digest of soybean 3 g/L, dextrose 2.5 g/L, sodium chloride 5 g/L, dipotassium phosphate 2.5 g/L) in 50 mL tubes under shaking conditions (150 rpm) for 3 days to prepare seed cultures, which were grown until reaching an $OD_{600}$ of 1.0.

For inoculation onto pine seedlings, each seed culture was diluted to an $OD_{600}$ of 0.1 using *T. matsutake* broth (TMB). The diluted strains were then mixed in equal volumes, resulting in a final volume ratio of 2:1 for the *Paenibacillus cineris* to the *Micrococcus* sp., and a total culture volume of 500~700 mL was prepared.

Preparation Example 3: Preparation of the Mixed Inoculum Containing *T. matsutake* Mycelium and the Microbial Pellets The seed cultures of the bacterial strains diluted to $OD_{600}$=0.1 according to Preparation Example 2, were centrifuged at 4,000 rpm for 10 minutes, and the supernatant was discarded to obtain microbial (bacterial) pellets. The pellets were then thoroughly mixed with the *T. matsutake* mycelium culture solution (500~700 mL) prepared according to Preparation Example 1. For inoculation onto pine seedlings, the mixed inoculum was prepared such that 500 mL of inoculum contained 30~70 g (wet weight) of *T. matsutake* mycelium and bacterial pellets corresponding to $OD_{600}$=0.1.

Example 3: Pine Seedling Inoculation Test (Analysis of *T. matsutake* Mycelium Inoculation Rate Enhancement)

The pine seedling inoculation test was conducted using three groups: a treatment group (co-inoculated with *T. matsutake* mycelium and the microbial pellets), a control group (treated with *T. matsutake* mycelium only, without microbial pellets), and an untreated group. A total of 100 one-year-old cultivated pine seedlings were prepared for the experiment. Eighty of the cultivated pine seedlings had their nursery soil removed, and their roots were washed at least three times with tap water. To facilitate inoculation, the roots were pruned to a length of 16 cm, and sufficient moisture was maintained to prevent the root tips from drying out. The remaining 20 seedlings were similarly pruned and kept moist, and were used as the untreated group.

For inoculation of the pine seedlings, the treatment group was inoculated with a mixture of the microbial pellets and *T. matsutake* mycelium culture prepared in Preparation Example 3, while the control group was inoculated with *T. matsutake* mycelium cultured prepared in Preparation Example 1.

Figures 5, 6:
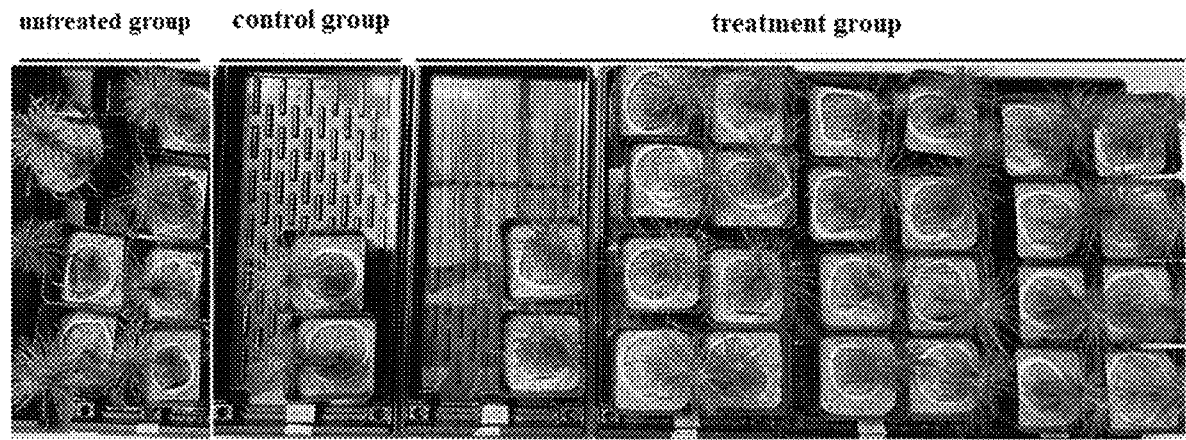
FIG. 5 is a photograph showing the planted pine seedlings inoculated according to the present invention.
FIG. 6 shows a schematic diagram of primer positions and PCR conditions for evaluating the inoculated pine seedlings.

For the treatment group, 60 of the pruned pine seedlings were submerged in the inoculum prepared in Preparation Example 3 for 30 minutes, ensuring that the roots were fully immersed. The seedlings were then planted in 20-cell culture pots containing a growth medium composed of a 4:1 (v: v) mixture of Masato (sandy loam soil) and perlite. The seedlings were watered twice a week, and an additional 10 mL of the inoculum was poured around the roots twice at two-week intervals (see FIG. 5).

For comparison, in the control group, 20 of the pruned pine seedlings were submerged in the *T. matsutake* culture solution prepared in Preparation Example 1 for 30 minutes, ensuring that the roots were fully immersed, and then planted in the same type of culture pots. The seedlings were watered twice a week, and an additional 10 mL of the *T. matsutake* culture solution was poured around the roots twice at two-week intervals to provide supplementary inoculation.

Twenty (20) untreated pine seedlings, which were not inoculated with either *T. matsutake* mycelium or the microbial pellets, were also planted in the same type of culture pots.

All planted pine seedlings were grown in a glass greenhouse under controlled conditions with a temperature of 25~30° C. and 50% humidity. After 7 months, the pine seedlings were transplanted into larger pots (size: 115 mm×115 mm×160 mm), and the presence or absence of *T. matsutake* inoculation was confirmed using *T. matsutake*-specific primers as listed in Table 3.

TABLE 3

| Primer name | Sequence (5'-3') | SEQ ID No. |
|---|---|---|
| DTm3_2001_F3 | AATATGTCTCGAGGAAG CTCGGTTTGAG | 8 |
| DTm3_2001_R3 | AGCCTGCAACAACTCCC AAAATCC | 9 |

Figure 7:
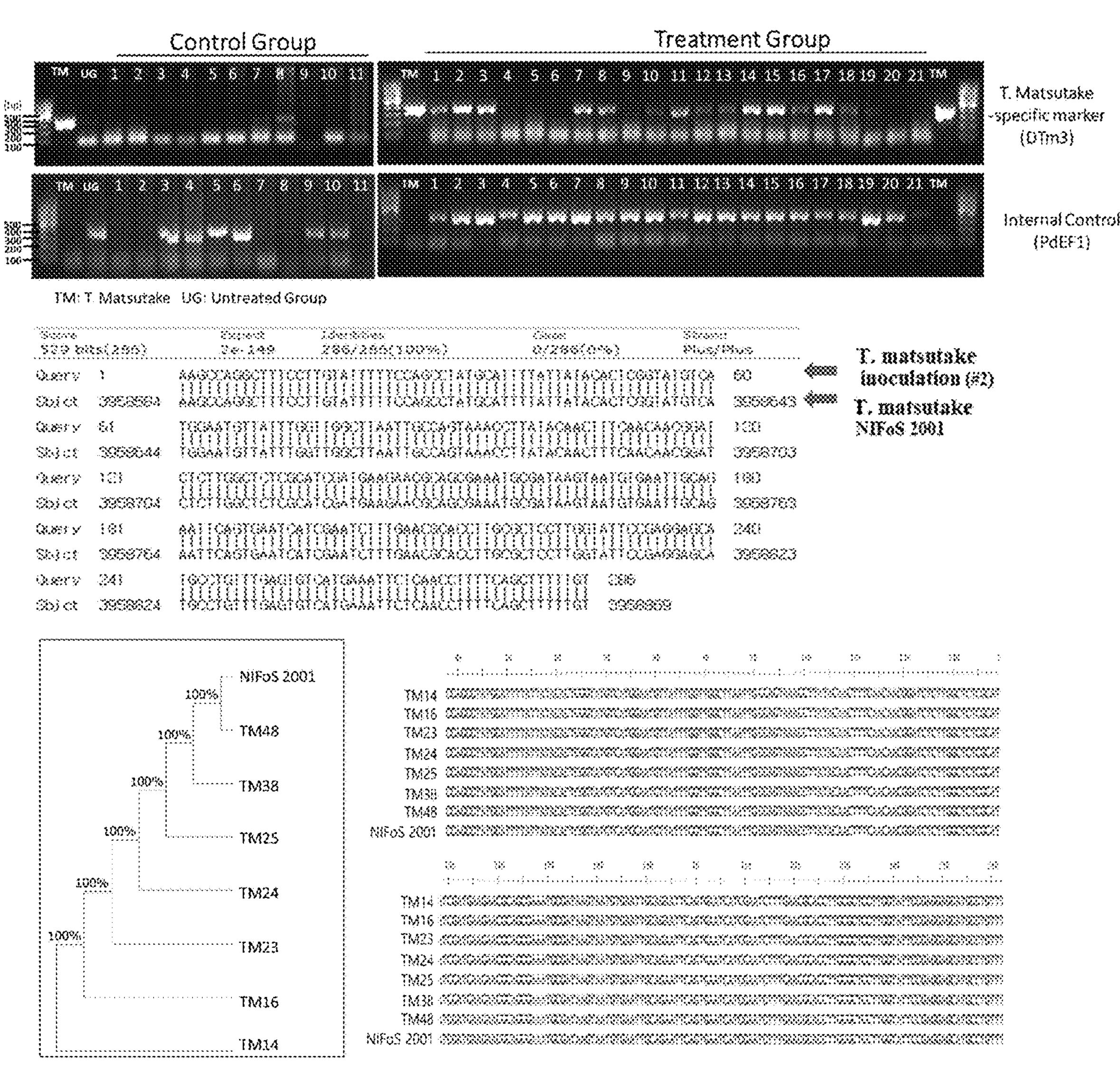
FIG. 7 shows the PCR analysis results of the inoculated pine seedlings.

Specifically, seven months after planting, portions of the roots from the surviving inoculated pine seedlings were excavated, and genomic DNA (gDNA) was extracted. Genomic DNA (gDNA) was extracted using the Qiagen Plant DNeasy kit and the CTAB manual method. DTm3_2001 primers were designed based on the ITS sequence of *T. matsutake* (NIFoS 2001) (Table 3), and PCR was performed under the conditions shown in FIG. 6 to amplify the target region from each gDNA sample. To confirm gDNA quality, the *Pinus densiflora* translation initiation factor gene (Pd_EF1) was used as an internal control. The results are shown in FIG. 7 and Table 4.

TABLE 4

| Group | Colonization rate |
|---|---|
| Treatment group (*T. matsutake* + bacterial strains) | 41.2 ± 4.0% |
| Control group (*T. matsutake* only) | 9.2 ± 1.2% |

As shown in Table 4, the inoculation rate (success rate) of *T. matsutake* in the control group, which was inoculated with *T. matsutake* alone without the bacterial strains of the present invention, was only 9.2±1.2% (range: 8.0~10.4%). In contrast, the inoculation rate of *T. matsutake* in pine seedlings co-inoculated with the bacterial strains according to the present invention was 41.2±4.0% (range: 37.2~45.2%), representing an average increase of approximately 4.5-fold (range: ~3.6~5.7-fold).

Seven months after planting, the number and survival rate of the inoculated pine seedlings were calculated, and the results are shown in Table 5.

TABLE 5

| Group | Survival rate |
|---|---|
| Treatment group (*T. matsutake* + bacterial strains) | 84.2 ± 1.2% |
| Control group (*T. matsutake* only) | 52.5 ± 3.5% |
| Untreated group | 32.5 ± 3.5% |

As shown in Table 5, the survival rate of the control group, which was inoculated with *T. matsutake* only without the bacterial strains of the present invention, was 52.5±3.5%. In contrast, the survival rate of the inoculated pine seedlings in the treatment group co-inoculated with the bacterial strains according to the present invention was 84.2±1.2% (range: 83~85.4%), representing an increase of approximately 1.5~1.7-fold.

INDUSTRIAL APPLICABILITY

Therefore, the microbial composition of the present invention, as well as the method for producing pine seedlings inoculated with *T. matsutake* mycelium, can significantly enhance the inoculation of *T. matsutake* mycelium in trees without causing environmental pollution or exhibiting toxicity to humans. By supplying the inoculated seedlings of the present invention on a large scale, efficient *T. matsutake* cultivation can be enabled for domestic pine mushroom farms, thereby ensuring stable income.

What is claimed is:

1. A method for producing *T. matsutake* mycelium-inoculated seedlings, comprising the steps of:

i) preparing a *T. matsutake* mycelium culture solution by liquid culturing the *T. matsutake* mycelium and homogenizing the culture using a homogenizer;

ii) culturing *Paenibacillus cineris* and *Micrococcus* sp. and centrifuging the cultures to obtain microbial pellets;

iii) washing and pruning the roots of pine seedlings;

iv) immersing the roots of the root-pruned pine seedlings in a mixed solution prepared by mixing the *T. matsutake* mycelium culture solution of step (i) and the microbial pellets of step (ii) to inoculate the seedlings; and v) planting the inoculated pine seedlings in soil and cultivating them.

2. The method according to claim 1, further comprising:

vi) an additional inoculation step in which, after planting the pine seedlings in soil, the mixed solution of the *T. matsutake* mycelium culture obtained in step (i) and the microbial pellets obtained in step (ii) is poured around the roots.

3. The method according to claim 1, wherein the inoculation rate of the inoculated seedlings is 37.2~45.2%, and the survival rate after inoculation is 84.2±1.2%.

4. The method according to claim 1, wherein in step ii), the microbial pellet is a mixture of *Paenibacillus cineris* and *Micrococcus* sp. at a volume ratio of 2:1 to 1:2.

5. The method according to claim 1, wherein in step ii), the microbial pellet is a mixture of *Paenibacillus cineris* and *Micrococcus* sp. at a volume ratio of 2:1.

* * * * *